(12) United States Patent
Walak

(10) Patent No.: US 7,168,605 B2
(45) Date of Patent: Jan. 30, 2007

(54) MICROTUBES FOR THERAPEUTIC DELIVERY

(75) Inventor: Steven Walak, Natick, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 655 days.

(21) Appl. No.: 09/954,179

(22) Filed: Sep. 18, 2001

(65) Prior Publication Data

US 2003/0055407 A1  Mar. 20, 2003

(51) Int. Cl.
*B21D 39/04* (2006.01)

(52) U.S. Cl. .................... 228/131; 228/193; 604/891.1

(58) Field of Classification Search ................ 228/131, 228/193, 247; 219/121.64; 428/36.9, 338, 428/339

See application file for complete search history.

(56) References Cited

U.S. PATENT DOCUMENTS

| | | | |
|---|---|---|---|
| 4,921,475 A | 5/1990 | Sibalis ..................... 604/20 |
| 5,035,711 A | 7/1991 | Aoki et al. .................... 623/11 |
| 6,090,363 A | 7/2000 | Green et al. | |
| 6,102,933 A | 8/2000 | Lee et al. | |
| 6,113,722 A | 9/2000 | Hoffman et al. ............ 156/155 |
| 2003/0055407 A1 | 3/2003 | Walik | |
| 2003/0093107 A1* | 5/2003 | Parsonage et al. .......... 606/194 |
| 2003/0143350 A1* | 7/2003 | Jimenez ...................... 428/35.2 |
| 2003/0198681 A1* | 10/2003 | Short et al. ................. 424/491 |

FOREIGN PATENT DOCUMENTS

| | | |
|---|---|---|
| WO | WO 02 060506 | 8/2002 |
| WO | WO 02 062968 | 8/2002 |

OTHER PUBLICATIONS

Baughman et al., "Carbon Nanotubes—the Route Toward Applications," Science, vol. 297, Aug. 2, 2002; pp. 787-792.
"Carbon Nanotube Bucky Paper Scaffold for Retinal Cell Transplantation," http://ettc.usc.edu/ames/nano/TOA-AME_BuckyPaper6.pdf, no date avail.
Antipov et al., "Sustained Release Properties of Polyelectrolyte Multilayer Capsules," J. Phys. Chem. B 2001, 105, 2281-2284.
Qiu et al., "Studies on the Drug Release Properties of Polysaccharide Multilayers Encapsulated Ibuprofen Microparticles," Langmuir 2001, 17, 5375-5380.
Decher et al., "Multilayer Thin Films," ISBN 3527304401, Chap. 13.2.1.2, no date avail.
Hird et al., "Supramolecular Structures of Novel Carbohydrate-Based Phospholipids," J. Am. Chem. Soc., 2000, 8097-8098.
Brannon-Peppas, "Polymers in Controlled Drug Delivery," Medical Plastics and Biomaterials Magazine, originally published Nov. 1997.
Byrne et al., "Use of Commercial Porous Ceramic Particles for Sustained Drug Delivery," International Jounral of Pharmaceutics 246 (2002) 61-73.

Joschek et al., "Chemical and Physicochemical Characterization of Porous Hydroxyapatite Ceramics Made of Natural Bone," Biomaterials 21 (2000) 1645-1658.
Zhang et al., "Crystallization and Microstructure Analysis of Calcium Phosphate-Based Glass Ceramics for Biomedical Applications," Journal of Non-Crystalline Solids 272 (2000) 14-21.
Ausman et al., "Organic Solvent Dispersions of Single-Walled Carbon Nanotubes: Toward Solutions of Pristine Nanotubes," J. Phys. Chem. B, 2000 104, 8911-8915.
Sreekumar, et al., "Single-Wall Carbon Nanotube Films," Chem. Mater, 2003, 15, 175-178.
Adriance-Mejia et al., "Alternative Formulations for the Anti-cancer Drug Paclitaxel (Taxol)," http://otc.isu.edu/-ndas/Term%20Papers%202002/Paclitaxel%20Formulations.pdf, no date avail.
Spinks et al., "Pneumatic Actuator Response from Carbon Nanotube Sheets," presented on the MRS Fall meeting 2001.
Liu et al., "Fullerene Pipes," Science, 280 (1998), 1253-1256.
Bos, "Albumin-Heparin Matrices Loaded with Growth Factor as Substrates For Endothelial Cell Seeding," Thesis—University of Twente, Enschede, The Netherlands, no date avail.
Georgakilas et al., "Organic Functionalization of Carbon Nanotubes," J. Am. Chem. Soc. 124 (5) (2002), 760-761.
Chen et al., "Plasma Activation of Carbon Nanotubes for Chemical Modification," J. Phys. Chem. B 2001, 105, 618-622.
Pantarotto et al., "Synthesis, Structural Characterization, and Immunological Properties of Carbon Nanotubes Functionalized with Peptides," J. Am. Chem. Soc. 2003, 125, 6160-6164.
Dettlaff-Weglikowska et al., "Chemical Functionalization of Single Walled Carbon Nanotubes," Current Applied Physics 2 (2002) 497-501.
Bahr et al., "Functionalization of Carbon Nanotubes by Electrochemical Reduction of Aryl Diazonium Salts: A Bucky Paper Electrode," J. Am. Chem. Soc. 2001, 123, 6536-6542.
Chen, et al, "Cyclodextrin-Mediated Soft Cutting of Single-Walled Carbon Nanotubes," J. Am. Chem. Soc. 2001, 123, 6201-6202.
Chen et al., "Solution Properties of Single-Walled Carbon Nanotubes," Science, 1998, 282, 95-98.
Chen et al, "Dissolution of Full-Length Single-Walled Carbon Nanotubes," J. Phys. Chem. B 2001, 105, 2525-2528.
Sun et al., "Soluble Dendron-Functionalized Carbon Nanotubes: Preparation, Characterization, and Properties," Chem. Mater. 2001, 13, 2864-2869.

(Continued)

*Primary Examiner*—Jonathan Johnson
(74) *Attorney, Agent, or Firm*—Kenyon & Kenyon LLP

(57) ABSTRACT

A medical implant that delivers therapeutic via microtubes and a method of making the same is provided. In one embodiment a biologically implantable structure adapted to fit within the body of a patient is provided. This structure may have a plurality of individual microtubes in physical communication with its outer surface, the microtubes containing or carrying a therapeutic. In an alternative embodiment a method of manufacturing an implantable medical appliance is provided. This method includes placing a pliant stratum of microtubes onto a biologically implantable medical structure and then applying a therapeutic to the pliant stratum to cover or fill the microtubes.

15 Claims, 8 Drawing Sheets

OTHER PUBLICATIONS

Bahr et al., "Dissolution of Small Diameter Single-Wall Carbon Nanotubes in Organic Solvents," Chem. Commun. 2001, 193-194.

Wong et al., "Covalently-Functionalized Single-Walled Carbon Nanotube Probe Tips for Chemical Force Microscopy," J. Am. Chem. Soc., 1998, 120, 8557-8558.

Holzinger et al., "Sidewall Functionalization of Carbon Nanotubes," Angew. Chem. Int. Ed., 2001, 40, 4002-4005.

Zhao et al., "Chromatographic Purification and Properties of Soluble Single-Walled Carbon Nanotubes," J. Am. Chem. Soc., 2001, 123, 11673-11677.

Chen et al., "Room-Temperature Assembly of Directional Carbon Nanotube Strings," J. Am. Chem. Soc., 2002, 124, 758-759.

Diehl et al., "Self-Assembled, Deterministic Carbon Nanotube Wiring Networks," Angew Chem. Int. Ed., 2002, 41, 353-356.

Krasheninnikov et al., "Ion-Irradiation-Induced Welding of Carbon Nanotubes," Physical Review B 66, 245403 (2002).

Fisher et al., "Carbon Nanotubes Literature Review," Department of Mechanical Engineering, Northwestern University, Feb. 21, 2001.

Final Report, Nanotechnology Workshop: From the Laboratory to New Commercial Frontiers, Rice University, Houston, Texas, May 23, 2002.

Henry, "Special Delivery—Alternative Methods for Delivering Drugs Improve Performance, Convenience, and Patient Compliance," Chemical & Engineering News, vol. 78, No. 38, Sep. 18, 2000, pp. 49-65.

"Antibody Coated Stent A Breakthrough in Cardiovascular Treatment," ScienceDaily New Release, May 22, 2003.

Klein-Soyer et al., "CD9 Participates in Endothelial Cell Migration During In Vitro Wound Repair," Arterioscler Thromb Vasc Biol., Feb. 2000, pp. 360-369 (http://www.atvbaha.org).

Hertel et al., "Manipulation of Individual Carbon Nanotubes and Their Interaction with Surfaces," J. Phys. Chem. B 1998, 102, 910-915.

P. X., Ma, et al, "Microtublar architecture of biodegradable polymer scaffolds", Journal of Biomedical Materials Research, Sep. 15, 2001, pp. 469-477, vol. 56, No. 4.

N. J. Meilander, et al., "Lipid-based microtublar drug delivery vehicles", Journal of Controlled Release, Mar. 12, 2001, pp. 141-152. vol. 71, No. 1.

* cited by examiner

MICROTUBES FOR THERAPEUTIC DELIVERY

TECHNICAL FIELD

The present invention regards the delivery of therapeutic to a target site. More specifically, the present invention regards the use of therapeutic laden microtubes, implanted near or at a target site, to deliver therapeutic to a target site of a patient.

BACKGROUND

The delivery of therapeutic to a target site is an oft-repeated procedure in the practice of contemporary medicine. Therapeutic may be delivered to a target site through direct injection as well as through implants that somehow carry the therapeutic. Implants that are used to deliver therapeutic may serve several purposes including reinforcing fatigued lumens and bridging ruptured vessels. In each of these cases the therapeutic being delivered may not only facilitate the short term healing associated with the introduction of the implant, but may, also, provide long term delivery of therapeutic to the surrounding areas.

One example of an implant is an expandable stent. Expandable stents are tube-like medical implants designed to support the inner walls of a patient's lumen. They can be self-expanding or, alternatively, may require external forces to expand them. In either case they are often deployed through the use of a catheter of some kind.

Because of the direct contact of the stent with the inner walls of the lumen, stents have been coated with various compounds and therapeutics to enhance their effectiveness. When this coating is haphazardly applied or has somehow been removed during the stent's manufacture or delivery the stent's effectiveness can be compromised because a uniform dosage of therapeutic from the coating of the stent to its surroundings may not be plausible.

SUMMARY OF THE INVENTION

A medical implant that delivers therapeutic via microtubes and a method of making the same is provided. In one embodiment a biologically implantable structure adapted to fit within the body of a patient is provided. This structure may have a plurality of individual microtubes in physical communication with its outer surface, the microtubes containing or carrying a therapeutic.

In an alternative embodiment a method of manufacturing an implantable medical appliance is provided. This method includes placing a pliant stratum of microtubes onto a biologically implantable medical structure and then applying a therapeutic to the pliant stratum to cover or fill the microtubes.

DETAILED DESCRIPTION

Figure 1:
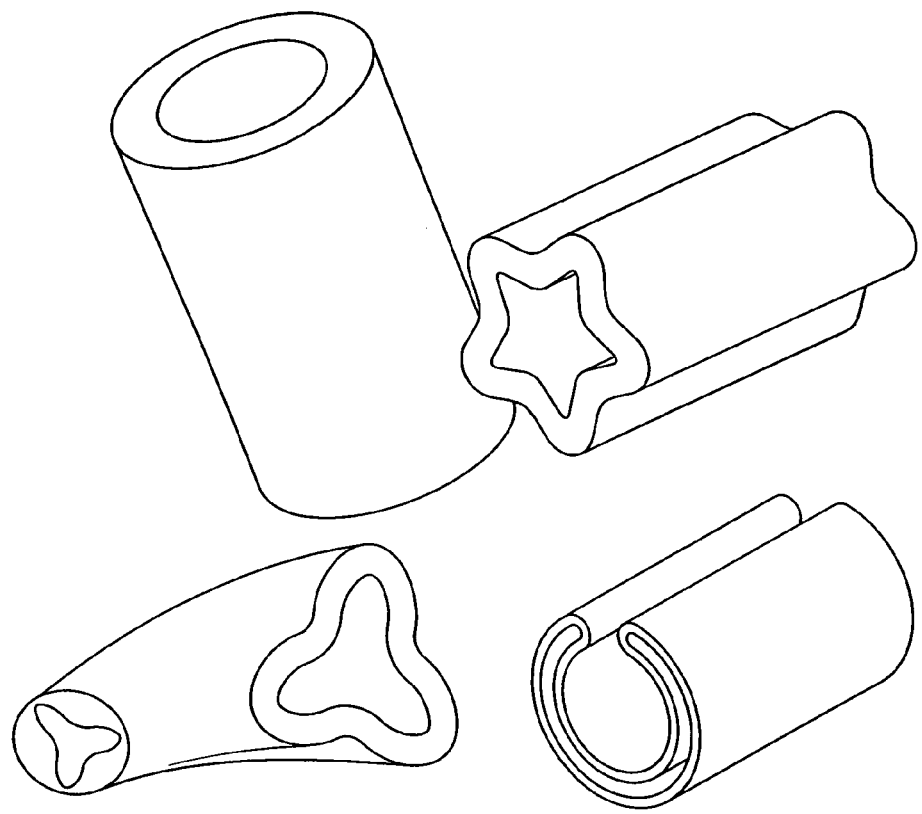
FIG. 1 is an enlarged cross-sectional view of five microtubes as may be employed in the present invention.

FIG. 1 provides an illustration of an enlarged cross-sectional view of several different microtubes as may be used in various embodiments of the present invention. As can be seen in FIG. 1, microtubes may be sized to be smaller than a human hair, being a few tens of microns in diameter, and may be constructed with various cross-sectional configurations, including U-, Y-, star-, and oval-shaped cross-sections. The microtubes may be hollow closed vessels, sleeves having one or more open ends, and solid structures. The microtubes in FIG. 1 are illustrated as being hollow with at least one open end. The microtubes may be made from a number of materials including metals, ceramics, and hard carbon. One advantage of employing microtubes in accord with the present invention is the increased surface area associated with their use.

Figure 2:
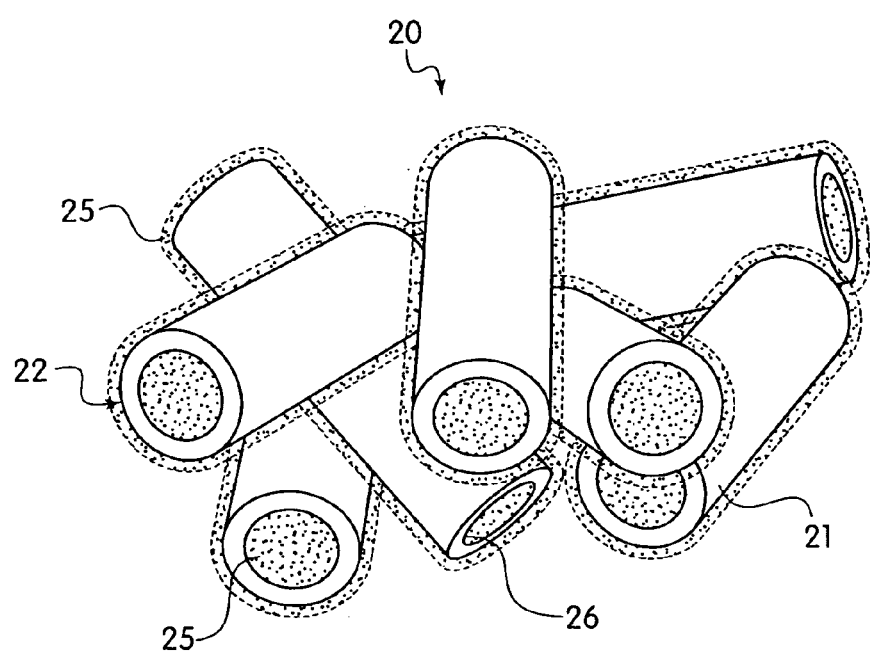
FIG. 2 is an enlarged perspective view of a pliant stratum of microtubes covered in and containing a therapeutic in accord with an embodiment of the present invention.

FIG. 2 provides an enlarged view of a pliant stratum 20 of microtubes 21 having a therapeutic 25 coating both the inner 26 and outer 22 surfaces of microtubes 21. In this embodiment, the microtubes 21 have a circular cross-section although they may also have any other desired cross-section, including those shown in FIG. 1. The microtubes 21 are enmeshed with each other so that they form a pliant stratum 20. This pliant stratum 20 may behave as a felt-like mat being pliable and moldable. The microtubes 21 may be positioned randomly with respect to each other in this embodiment as illustrated FIG. 2. Alternatively, they may be arranged in some sort of pattern to create the pliant stratum 20. In either situation, it is preferable that the microtubes be enmeshed such that they interact with and support one another so as to substantially behave as a single structure or unit.

The therapeutic 25 may be applied to the microtubes 21 by soaking the microtubes until the therapeutic 25 coats or infiltrates the microtubes 21. The microtubes 21 may be positioned next to each other in a such a manner as to create voids or spaces between them. These voids or spaces may be filled with therapeutic by dipping the stratum of microtubes 21 in a therapeutic and allowing the therapeutic to wick up into and around the microtubes 21.

Figure 3:
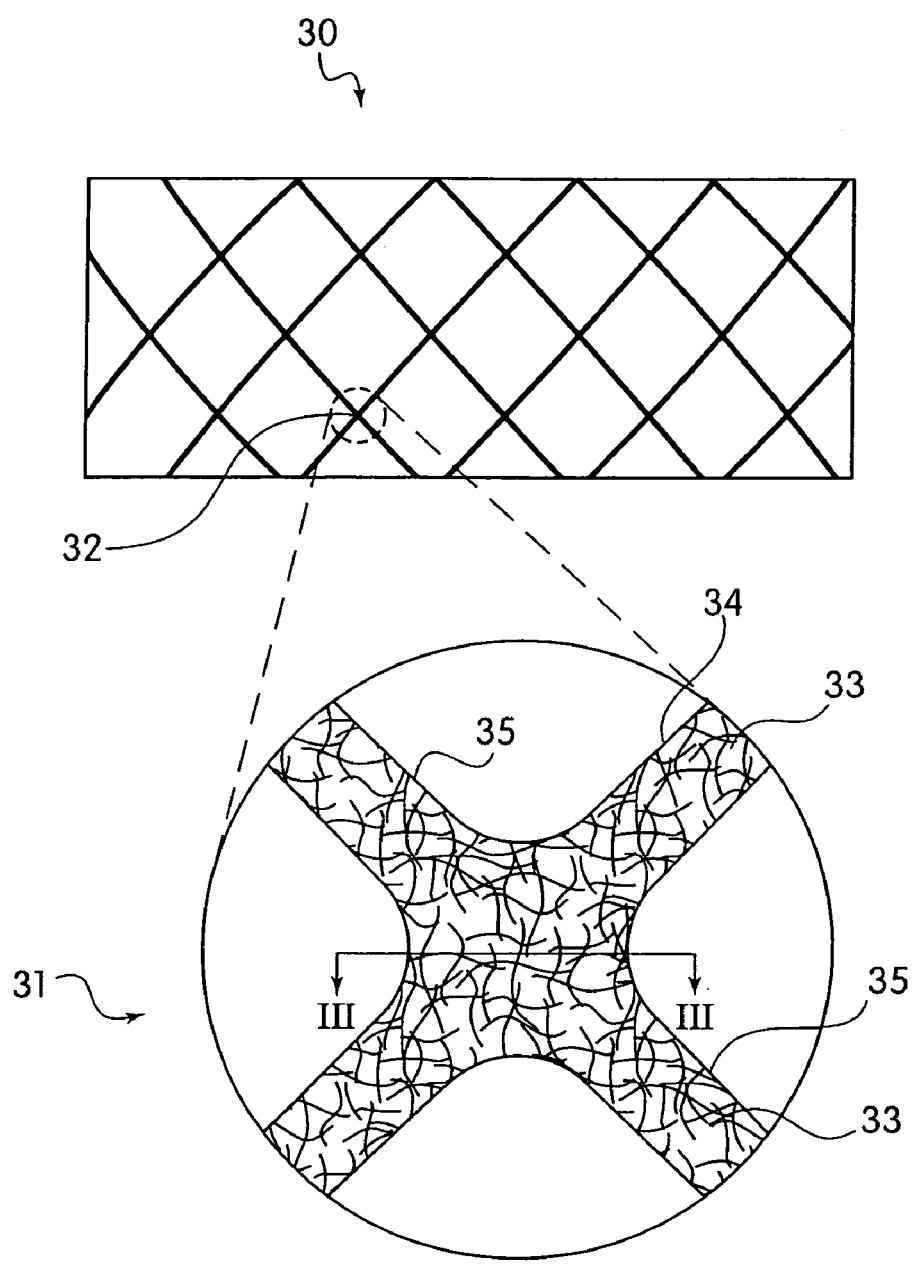
FIG. 3 is a side view of a stent covered with a pliant stratum of microtubes, the Figure having an enlarged portion to highlight the microtubes attached to the stent, all in accord with another embodiment of the present invention.

FIG. 3 is a side view of a stent 30 covered with microtubes 33 as may be employed in an alternative embodiment of the present invention. The enlarged portion 31 of FIG. 3 illustrates the junction point of two struts 35 of the stent 30 that have been covered with microtubes 33. As can be seen in FIG. 3 the microtubes 33 may completely cover the struts 35 of the stent 30 and may also extend out past the struts 33 as indicated by numeral 34. By completely covering the struts 35 therapeutic carried by the microtubes 33 may be more uniformly released to a target site in the body.

When the implant is expandable or otherwise reconfigurable, it is preferable to secure the pliant stratum to points on the implant that will deflect or move the least during the implant's reconfiguration. By securing the stratum to these minimal deflection points the magnitude of the forces that will be placed on the stratum during the implants reconfiguration may be reduced. By reducing the forces during reconfiguration the likelihood that the stratum will be dislodged, impaired or otherwise destroyed during reconfiguration may be reduced. In the embodiment of FIG. 3 the stratum may be secured to the struts 35 near the joints 32 to reduce the forces that may be placed on the stratum by the stent during the expansion of the stent 30.

Figure 4:
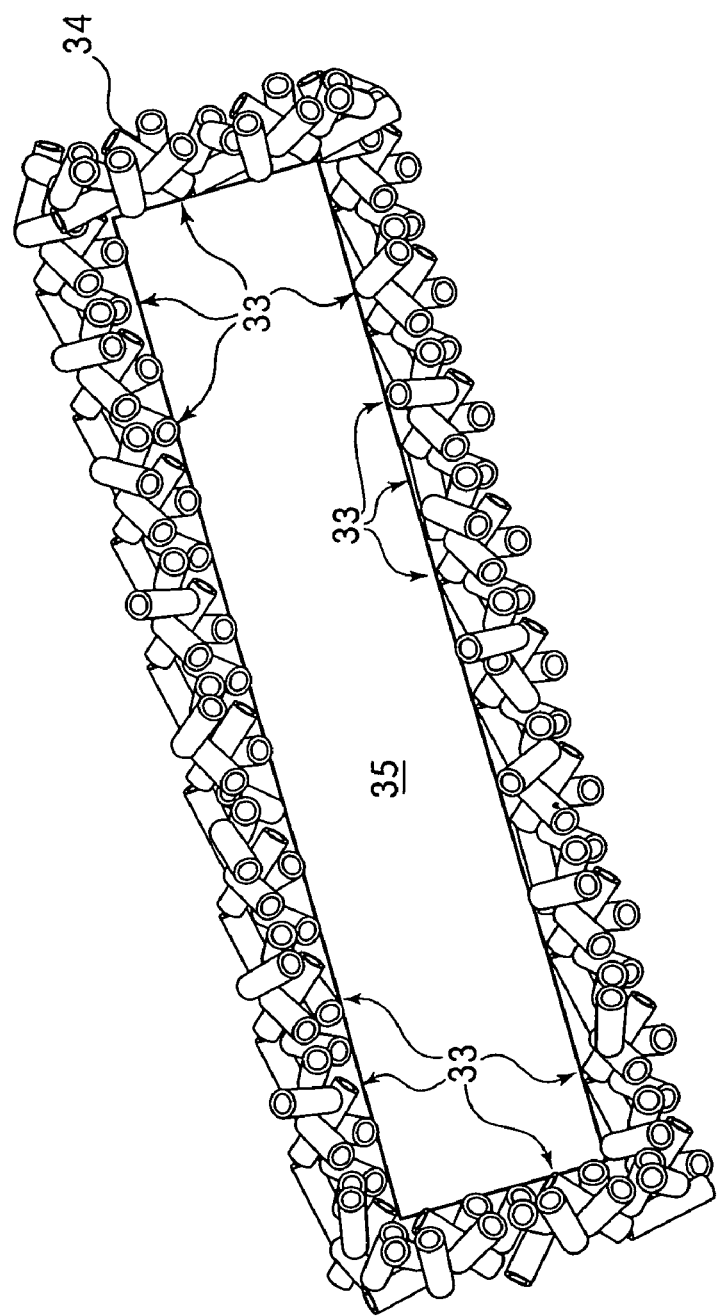
FIG. 4 is an enlarged cross-sectional view taken along line III—III of FIG. 3.

FIG. 4 is an enlarged cross-sectional view taken along line III—III of FIG. 3. In FIG. 3 the strut 35 has been completely coated with a stratum of pliant microtubes 33. Although the microtubes 33 are cylindrical in shape in this figure, they could have numerous other shapes including those illustrated in FIG. 1. The microtubes 33 do not create a smooth external surface in this embodiment but, rather, create a rough profile dictated by the random orientation of the microtubes 33 on the strut 35.

The microtubes 33 in this embodiment may be attached to stents or other appliances using various attachment methods. One of these methods would include heating the microtubes and the stent's struts while they were in contact with each other. Here, the molecules or atoms of the struts and the microtubes may intermingled due to thermal agitation, thereby diffusion bonding the microtubes to the struts. Metallic microtubes may also be attached to the stent by brazing with a biocompatible brazing material such as gold. Alternatively, the microtubes may be mixed into an electrolytic plating material, such as gold, that may then be used to surface plate the stent. Laser or resistance welding may also be used to affix the pliant stratum to the implant. One advantage of laser welding is that it may allow for pinpoint securement of the stratum to the implant. Microtubes may also be attached to the implant using a pressurized thermal bonding process or polymer adhesive.

In another embodiment, rather than creating a pliant stratum and then applying it to an implant, the microtubes may simply be sprayed directly onto the implant or the implant may be dipped into a vat of polymer or other coating that contains the microtubes.

Figure 5:
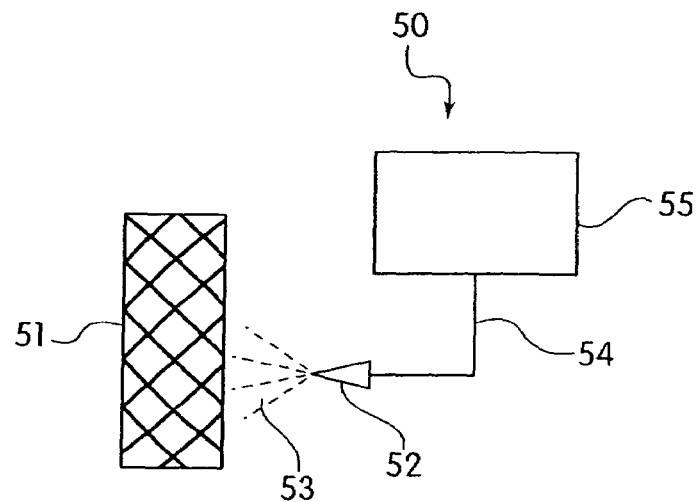
FIG. 5 is a view of a system for applying a therapeutic to cover and fill microtubes dispersed over stent in accord with another embodiment of the present invention.

FIG. 5 shows a system 50 that may be used to coat a stent 51 with therapeutic laden microtubes 53 in accord with alternative embodiment of the present invention. This system 50 may employ a reservoir 55, a line 54, and a nozzle 52 in fluid communication with the reservoir 55 via the line 54. In this embodiment a therapeutic 53, or a mixture of microtubes and polymer adhesive, may be held in the reservoir 55, and may be sprayed at the workpiece 51 in order to coat the workpiece 51. Polymer adhesives suitable for such coatings include silicones, (e.g. polysiloxanes and subsitutes polysiloxanes), polyurethanes (including polycarbonate urethanes), thermoplastic elastomers in general, ethylene vinyl acetate copolymers, polyolefin elastomers, ethylene-propylene terpolymer rubbers, polyamide elastomers, polyolefin elastomers, and combinations thereof. If the workpiece had been previously coated with microtubes, a therapeutic based mixture may be stored and sprayed at the workpiece 51. Conversely, if the workpiece had not been previously treated, a mixture of microtubes and therapeutic may be sprayed at the workpiece 51.

Figure 6:
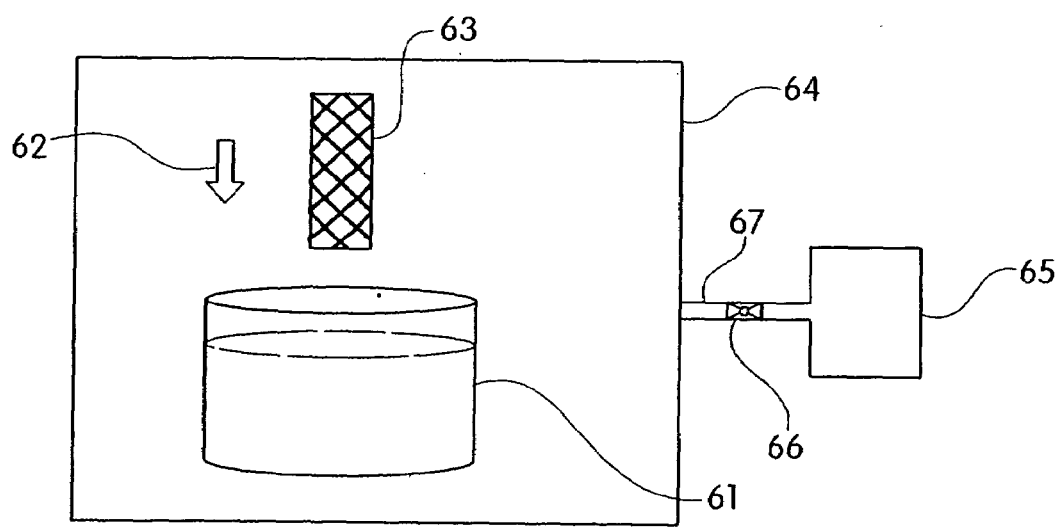
FIG. 6 is a view of system for applying a therapeutic to cover and fill the microtubes dispersed over a stent in accord with another embodiment of the present invention.

FIG. 6 shows a process of soaking a stent 63 previously coated with microtubes in accord with another alternative embodiment of the present invention. The coating process in this embodiment may be performed in a vacuum chamber 64 to facilitate the process and improve the wicking of the therapeutic into and around the microtubes already present on the stent 63. The vacuum force in this embodiment may be generated by using a vacuum pump 65 attached to the vacuum chamber 64 via a line 67 having a valve 66.

Figure 7:
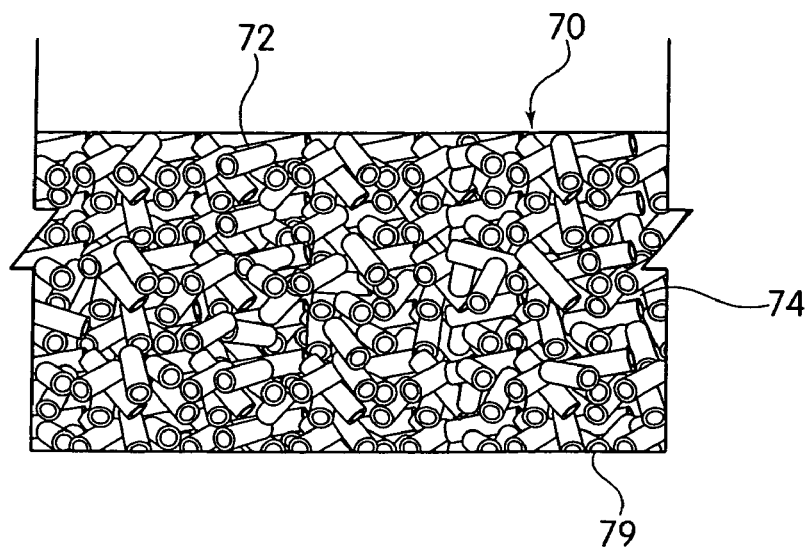
FIG. 7 is an enlarged view of microtubes dispersed in a polymer matrix as may be used to coat an implantable medical implant in accord with another embodiment of the present invention.

FIG. 7 provides an enlarged view of microtubes 72 surrounding or covering a surface of a workpiece 79. Here the microtubes 72 are dispersed in a polymer matrix 74, such as an epoxy, having a viscosity that prevents the matrix 74 from filling the microtubes. The polymer matrix 74 may also include poly methyl methacrylate, poly methyl pentane, poly ether ether ketone, liquid crystal polymers, polysulfones, polyimides and other suitable "hard" polymers with similar properties. The polymer matrix may be made from a single polymer or a composite of polymers. The microtubes 72 in this embodiment may provide additional structural support to the polymer matrix due to their interaction. In this embodiment the polymer matrix may harden to a substantially smooth surface 70 with some microtubes being exposed at the surface 70 after the matrix 74 has cured.

Figure 8:
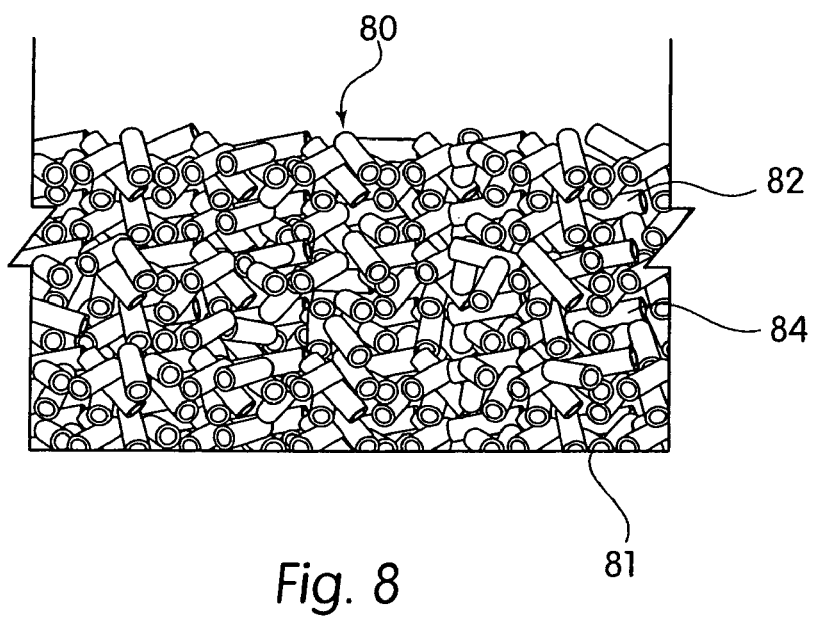
FIG. 8 is an enlarged view of abraded microtubes dispersed in a polymer matrix as may be used to coat a medical implant in accord with another embodiment of the present invention.

FIG. 8 provides an enlarged side view of abraded microtubes 82 dispersed in a high viscosity polymer matrix 84 in accord with another alternative embodiment of the present invention. The microtubes 82, is this embodiment, may be placed in a polymer before it is hardened. The surface 80 of the polymer may be abraded (as shown in FIG. 8) to uncover the open ends of the microtubes exposed at the surface 80 of the polymer matrix. Uncovering the ends of the microtubes through an abrasion process enables the microtubes to more effectively draw therapeutic into their internal lumens. In this embodiment, the microtubes provide additional structural support to the polymer matrix as well as facilitate the delivery of the therapeutic to a target site. Generally longer microtubes are desired in this embodiment.

Figure 9:
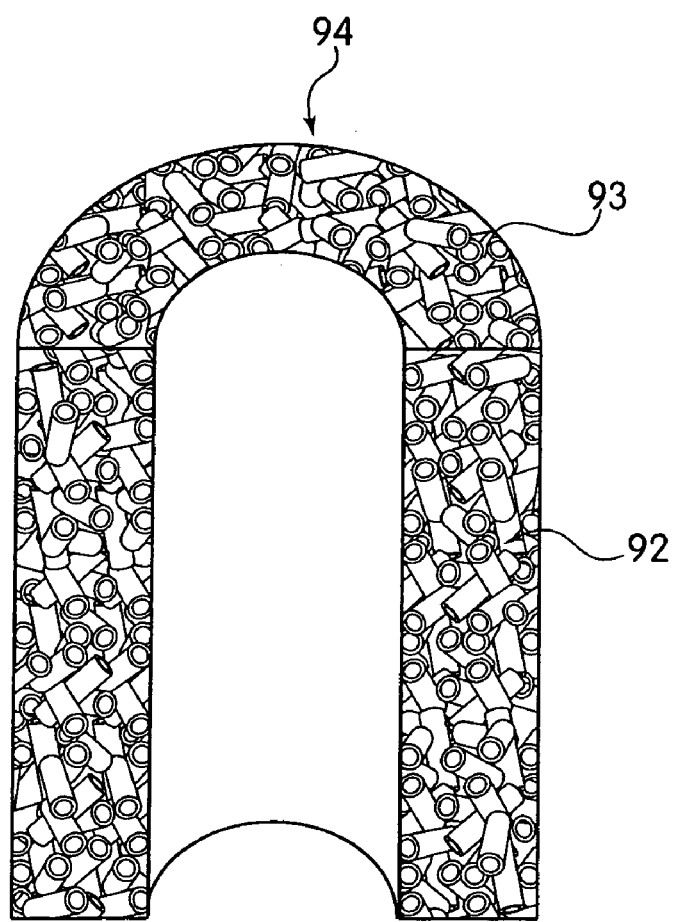
FIG. 9 is a cross-sectional view of a pliant layer of microtubes used to form a medical implant in accord with another embodiment of the present invention.

FIG. 9 provides a cross-sectional cutaway view of microtubes 92 dispersed in a high viscosity polymer matrix 93. Here the polymer matrix has been formed like a medical implant 94 such as a graft. In this embodiment, the microtubes 92, have a circular cross-section and are formed in the shape of a medical implant rather than being sprayed, dipped or otherwise applied to an implant as described above.

Figure 10:
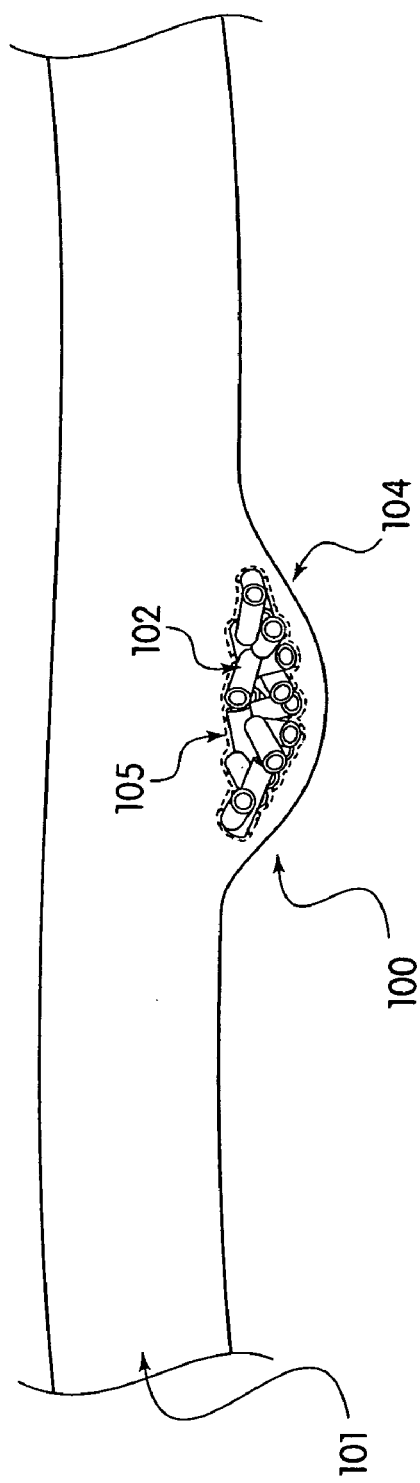
FIG. 10 is a cross-sectional view of a pliant layer of microtubes used as a medical implant in accord with another embodiment of the present invention.

FIG. 10 provides a side view of a pliant stratum 104 of microtubes 102 in accord with another embodiment of the present invention. In this embodiment, the pliant stratum 104 may be formed like a medical implant, such as an embolic agent 100 which fills an aneurism in an artery 101, and may be placed at the target site to deliver therapeutic to the target site. In other words, rather than providing the structural support of the stents described above, the present implant 104 simply delivers therapeutic to the target site without providing any additional structural benefits.

The microtubes 102 in this embodiment may be enmeshed with each other and sintered together to form a structural member such as a pliant stratum 104. The therapeutic 105 may be applied to the microtubes 102 by soaking or any other effective method. Once prepared, this implant may be inserted into the artery or other target site of the body for the short or long term delivery of therapeutic to the target site.

The medical implant described above may be any one of numerous medical implants including expandable stents, stent grafts, peripherally-inserted central catheters, (PICCs), arterioventricular shunts (a-v shunts), angio-catheters, embolic agents, vena cava filters, aneurism coils, implantable prostheses, and implantable fasteners. These implants, as well as others, may be carried to a target site within the body by a medical device and then deployed in order to provide medical relief or repair to the targeted site. They may also be deployed through more invasive procedures.

The implant in each of the above embodiments may also contain a tracer chemical to assist the practitioner positioning or otherwise deploying the implant. For example, when a tracer is employed an imaging system may be used to track the progress and position of a stent as it is snaked through a lumen in the body en route to reaching the target site.

The therapeutic can include pharmaceutically active compounds, nucleic acids with and without carrier vectors such as lipids, compacting agents (such as histones), virus (such as adenovirus, andenoassociated virus, retrovirus, lentivirus and a-virus), polymers, hyaluronic acid, proteins, cells and the like, with or without targeting sequences.

Examples of therapeutics used in conjunction with the present invention include, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/anti-proliferative/anti-mitotic agents such as paclitaxel, 5-fluorouracil, methotrexate, doxorubicin, daunorubicin, cyclosporine, cisplatin, vinbiastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chiormethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vasoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the injection site. The delivery medium is formulated as needed to maintain cell function and viability. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor $\alpha$ and $\beta$, platelet-derived endothelial growth factor, platelet-derived growth factor, tumor necrosis factor $\alpha$, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNAs encoding them.

A medical implant that delivers therapeutic via microtubes and a method of making the same is provided. The above-described embodiments are illustrative examples of the present invention. As will be evident to one of skill in the art, modifications to these embodiments as well as entirely new embodiments are plausible without departing from the spirit and scope of the present invention.

What is claimed is:

1. A method of manufacturing a medical implant comprising:

supplying a plurality of microtubes;

interfacing a pliant layer of microtubes with a biologically implantable medical structure; and applying a therapeutic to the pliant layer to cover a surface of one or more of the microtubes.

2. The method of claim 1 wherein interfacing the pliant layer of microtubes with a biologically implantable medical structure further comprises:

enmeshing the microtubes together to form the pliant layer; and coupling the pliant layer onto a surface of the biologically implantable medical structure.

3. The method of claim 2 wherein the method of coupling the pliant layer to a surface of a biologically implantable medical structure is one or more of diffusion bonding, metal working, sintering, brazing, plating, electrolytically attaching or welding.

4. The method of claim 1 wherein applying a therapeutic to the pliant layer further comprises:

activating a vacuum force to draw therapeutic into and among the microtubes forming the pliant layer.

5. The method of claim 1 wherein applying a therapeutic to the pliant stratum further comprises:

soaking the pliant layer of microtubes in a therapeutic.

6. The method of claim 1 wherein
the biologically implantable medical structure is expandable from a first configuration to a second configuration.

7. The method of claim 1 wherein
the biologically implantable medical structure is chosen from a group comprising:
a PICC, an embolic agent, an aneurysm coil, a stent-graft, an a-v shunt, vena cava filter and an angio-catheter.

8. The method of claim 1 wherein
a polymer is used to enmesh the microtubes into a pliable stratum.

9. The method of claim 1 wherein
an exterior surface of the pliable layer is abraded before applying the therapeutic.

10. The method of claim 1 wherein the microtubes are uniformly shaped.

11. The method of claim 2 wherein the pliant layer is shaped as a sleeve.

12. The method of claim 1 wherein at least one of the microtubes has an open end.

13. The method of claim 1 wherein at least one of the microtubes defines a channel having a first opening and a second opening.

14. The method of claim 1 wherein at least one of the microtubes has a cross-sectional area that varies over a longitudinal length of the microtube.

15. The method of claim 1 wherein at least one of the microtubes is hollow.

* * * * *

UNITED STATES PATENT AND TRADEMARK OFFICE
CERTIFICATE OF CORRECTION

PATENT NO. : 7,168,605 B2  
APPLICATION NO. : 09/954179  
DATED : January 30, 2007  
INVENTOR(S) : Steven Walak Page 1 of 1

It is certified that error appears in the above-identified patent and that said Letters Patent is hereby corrected as shown below:

Title Page, under item (56) Other Publications, Col. 2, line 17, change "on" to -- at --.

Col. 1 line 58, change "five" to -- four --.

Col. 2 line 4, before "stent" insert -- a --.

Col. 3 line 12, after "points" insert -- , --.
      line 15, after "reconfiguration" insert -- , --.
      line 35, change "intermingled" to -- intermingle --.
      line 62, change "substitutes" to -- substitute --.

Col. 4 line 6, after "microtubes" insert -- in tank 61 --.

Col. 5 line 20, change "andenoassociated" to -- adenoassociated --.

Col. 6 line 3, change "promotors" to -- promoters --.
    line 5, change "promotors" to -- promoters --.

Signed and Sealed this

Fifteenth Day of July, 2008

JON W. DUDAS  
*Director of the United States Patent and Trademark Office*